Patented Mar. 3, 1942

Plant Pat. 505

UNITED STATES PATENT OFFICE

505

ROSE

Josephine D. Brownell, Little Compton, R. I.

No Drawing. Application June 23, 1941,
Serial No. 399,421

1 Claim. (Cl. 47—61)

My invention relates to roses and especially to a new, original and distinct variety of the class known commercially as hardy climbing roses and to a subdivision thereof known as large flowering *Rosa wichuraiana* hybrid; and also a further subdivision known as hardy everblooming climbing roses; discovered by me and under my direction in my breeding grounds or gardens in Little Compton, Rhode Island, by cross pollinating, which can be and has been asexually reproduced.

My new rose is new as to the following characteristics as to their joint association in connection with the characteristics of hardiness and immunity from serious injury on account of cold temperatures prevailing in certain parts of the northern portion of the United States;

The unique orange toned color of the petals, being approximately spectrum orange (ordinary dictionary definition) in total effect of both sides of the petals;

The multiple petals and variation within certain definite limits of the form of the bloom;

Its character of fragrance;

Its climbing and branching habit;

And especially its habit of blooming continuously from early bloom time until frost.

This new rose variety is a variation or sport which occurred on a plant of the variety "Copper Glow," Plant Patent Number 458. The variation consisted in a change from once bloom climber character to an everblooming climber character. There was no change in the form or other character of the flower, the only change being a change in the blooming character from the once bloom character of the climber to the reblooming or ever blooming character common to the hybrid tea class of roses.

I otherwise describe my new rose as follows:

It is a large flowered hardy climbing hybrid *Rosa wichuraiana,* crossed in its ancestral generations with, in addition to *Rosa wichuraiana* several hydrid tea and species roses.

It is otherwise described as follows

Essential Information

*Type.*—Hardy climbing; outdoor; sport; for cut flowers, garden display and for pot forcing.

*Class.*—Hybrid climbing wichuraiana; subdivision, large flowered climber.

*Breeding or discovery.*—The discovery of this new rose was made by me and by my assistants and co-workers on the 15th day of August, 1939* in my garden; the bloom which first expressed this variation was cut and removed from the plant on which it grew and the eyes on the stem thereof were promptly budded on *Rosa multiflora* root stock under my direction and in my propagating fields. The following spring these eyes developed and grew, and contrary to the procedure in such cases with once bloom climber eyes, they set bloom stems which matured and bloomed flowers at the normal bloom time and during this same period also grew climber canes common to once bloom climbers. These plants continued throughout the season to rebloom and produce flowers in the manner common to the dwarf hybrid tea. Eyes from second clonal generation similarly budded produced flowers the same season; and eyes from such bloom stems budded have also produced bloom stems in the hybrid tea manner and canes in the once bloom climber manner. Thus these propagations have reproduced the character of rebloom originally discovered in the sport or variation described. The plant on which this new variation was produced was produced by me as described in Plant Patent 458.

From a genetic view point it is to be noted that this variation or bud sport is a change in the factors for vegetative and sexual expression. Normally the selection between vegetative and floral growth is determined under a more or less definite pattern. In this variation or sport that pattern is nullified by a variation to an indeterminate or more intricate pattern of selection of these expressions, by which the floral expression becomes constant. This type of expression is not common to the hybrid tea or to tall growing *Rosa wichuraiana* climber forms or to any recombination thereof through inheritance.

*Propagation.*—It has held its distinguishing characteristics through succeeding propagations by budding.

Flower

*Habit.*—It blooms out of doors in Little Compton, Rhode Island, in late June and July and begins to bloom about five days before the variety Mary Wallace begins to bloom.

*Flowers borne.*—Singly to eight, occasionally more; in regular hybrid tea type of clusters, which usually develop consecutively a few days' maturity apart, on strong stiff woody stems, varying in length up to 15 and 20 or more inches in length.

*Quantity of bloom.*—Abundant out of doors in full sunshine, not materially reduced by covering established plants with clean earth for winter protection. It blooms the year after budding when promptly transplanted.

*This and other dates herein are approximate.

*Continuity.*—Continuously from bloom time until heavy frost.

*Comparisons.*—The hardy climbing everblooming rose variety in commerce most closely resembling this new rose variety is New Dawn. This new rose is distinctly different from New Dawn in that New Dawn is of a shell pink, its petals are usually less recurled, and the new rose has fragrance of a more spicy nature. The bloom and rebloom habits are substantially the same.

I claim:

The hardy reblooming *Rosa wichuraiana* climbing rose sport variety characterized by the characteristics of the variety Copper Glow with the additional character of intensive constant rebloom until frost.

JOSEPHINE D. BROWNELL.